(12) United States Patent
Johansen et al.

(10) Patent No.: US 6,228,128 B1
(45) Date of Patent: May 8, 2001

(54) ANTIMICROBIAL ACTIVITY OF LACCASES

(76) Inventors: Charlotte Johansen, Vasevej 1, DK-2840 Holte; Anders Hjelholt Pedersen, Nybro Vaenge 58, DK-2800 Lyngby; Claus Crone Fuglsang, Poppelhoej 43, 2990 Nivaa, all of (DK)

( * ) Notice: Subject to any disclaimer, the term of this patent is extended or adjusted under 35 U.S.C. 154(b) by 0 days.

(21) Appl. No.: 09/184,419

(22) Filed: Nov. 2, 1998

Related U.S. Application Data

(62) Division of application No. 09/184,418, filed on Nov. 2, 1998.
(60) Provisional application No. 60/101,644, filed on Sep. 23, 1998.

(30) Foreign Application Priority Data

Nov. 10, 1997 (DK) .................................... 1273/97
Sep. 10, 1998 (DK) ............................. 1998 01144

(51) Int. Cl.$^7$ .............................. C12S 11/00; C11D 7/42
(52) U.S. Cl. .................. 8/137; 134/42; 422/28; 424/78.03; 424/78.07; 510/114; 510/131; 510/137; 510/161; 510/226; 510/320; 510/321; 510/392; 510/530
(58) Field of Search ................... 8/137; 134/42; 422/28; 424/78.07, 78.03; 510/114, 131, 137, 226, 161, 320, 321, 392, 530

(56) References Cited

U.S. PATENT DOCUMENTS

| | | |
|---|---|---|
| 4,370,199 | 1/1983 | Orndorff . |
| 4,478,683 | 10/1984 | Orndorff . |
| 5,837,505 * | 6/1999 | Della-Cioppa et al. .............. 435/128 |
| 5,912,405 * | 6/1999 | Schneider et al. ........................ 8/111 |
| 5,968,883 * | 10/1999 | Cherry et al. ........................ 510/305 |
| 5,972,042 * | 10/1999 | Barfoed et al. ........................... 8/401 |
| 5,985,818 * | 11/1999 | Svedsen et al. ...................... 510/392 |
| 6,036,729 * | 9/2000 | Barfoed et al. ........................... 8/401 |

FOREIGN PATENT DOCUMENTS

| | | |
|---|---|---|
| 40 08 894 | 9/1991 | (DE) . |
| 91610032 | 4/1991 | (EP) . |
| 0 500 387 | 8/1992 | (EP) . |
| WO 90/03987 | 4/1990 | (WO) . |
| WO 91/05839 | 5/1991 | (WO) . |
| WO 91/14820 | 10/1991 | (WO) . |
| WO 97/04127 | 3/1994 | (WO) . |
| WO 94/29510 | 12/1994 | (WO) . |
| WO 95/27046 | 10/1995 | (WO) . |
| WO 96/06930 | 3/1996 | (WO) . |
| WO 96/10079 | 4/1996 | (WO) . |
| WO 97/00038 | 1/1997 | (WO) . |
| WO 97/28257 | 8/1997 | (WO) . |
| 97/41215 * | 11/1997 | (WO) . |
| WO 97/41215 | 11/1997 | (WO) . |
| WO 97/42825 | 11/1997 | (WO) . |
| WO 97/43381 | 11/1997 | (WO) . |
| WO 97/43383 | 11/1997 | (WO) . |

OTHER PUBLICATIONS

Oshima et al., Japanese Abstract of JP 64–60693 (Apr. 1990).

* cited by examiner

*Primary Examiner*—Gregory R. Del Cotto

(57) ABSTRACT

A method for antimicrobial treatment of microorganisms and/or viruses which involves treating the microorganisms and/or viruses with an effective amount of a fungal laccase and one or more enhancers in the presence of oxygen, the enhancers having the formula:

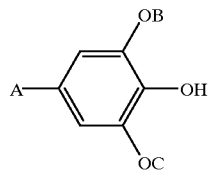

wherein A, B and C are as defined in the specification.

20 Claims, 5 Drawing Sheets

ANTIMICROBIAL ACTIVITY OF LACCASES

CROSS-REFERENCE TO RELATED APPLICATIONS

This is a 37 C.F.R. § 1.53(b) divisional application of U.S. Ser. No. 09/184,418 filed Nov. 2, 1998. The benefit of which is claimed under 35 U.S.C. 120.

This application claims priority under 35 U.S.C. 119 of U.S. provisional application 60/101,644 filed Sep. 23, 1998 and Danish application nos. PA 1998 01144 and 1273/96 filed Sep. 10, 1998 and Nov. 10, 1997, respectively, the contents of which are fully incorporated herein by reference.

FIELD OF THE INVENTION

The present invention relates to a method of antimicrobial treatment using a combination of a laccase enzyme and an enhancer capable of killing or inhibiting microorganisms, more specifically microorganisms present in laundry, on hard surfaces, on skin, teeth or mucous membranes; and for preserving food products, cosmetics, paints, coatings, etc., the composition comprising a laccase enzyme and an enhancing agent acting as an electron donor.

BACKGROUND OF THE INVENTION

Various enzymatic antimicrobial compositions are known in the art. For instance, WO 94/04127 discloses stabilized dentifrice compositions which are capable of producing antimicrobially effective concentrations of hypothiocyanite ions. The compositions contain an oxidase capable of producing hydrogen peroxide and a peroxidase enzyme capable of oxidizing thiocyanate ions, which are normally present in saliva, to antimicrobial hypothiocyanite ions. Suitable peroxidases include lactoperoxidase, myeloperoxidase, salivary peroxidase and chloro-peroxidase.

In EP-A-0 500 387 enzymatic antimicrobial compositions are disclosed comprising a haloperoxidase, e.g. myeloperoxidase, eosinophil oxidase, lactoperoxidase and chloroperoxidase, which selectively binds to and inhibits the growth of target microorganisms in the presence of peroxide and halide.

WO 95/27046 discloses an antimicrobial composition comprising a Vanadium chloroperoxidase, halide ions, and hydrogen peroxide or a hydrogen peroxide-generating agent. Laccase is an enzyme catalyzing the oxidation of substrates according to the general formula:

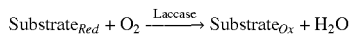

$$\text{Substrate}_{Red} + O_2 \xrightarrow{\text{Laccase}} \text{Substrate}_{Ox} + H_2O$$

The enzyme has been used in the paper and pulp industry (WO 94/29510, for bleaching purposes in laundry washing (WO 91/05839, EP 91610032, DE4008894, JP-A64-60693), but the use of the enzyme in for antimicrobial purposes was not suggested.

WO 96/10079 discloses a method for oxidizing a compound with a phenol oxidizing enzyme in the presence of an enhancer of the general formula:

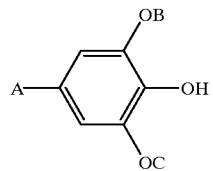

for bleaching dyes in solution.

WO 97/28257 and WO 97/00038 discloses a methods for inactivating a microorganism or virus with polyphenol oxidases derived from the bacterium of the genus Bacillus in the presence of oxygen and an enhancer.

The object of this invention is to provide a method for antimicrobial treatment of microbial cells or microorganisms, i.e. for disinfection or preservation, which is easy to use and an effective alternative to the known disinfecting and preserving methods.

SUMMARY OF THE INVENTION

Treatment of microorganisms and/or viruses comprising treating said microorganisms and/or viruses with an effective amount of fungal laccase enzymes and an effective amount of one or more enhancers in the presence of oxygen ($O_2$), the enhancer being of the formula:

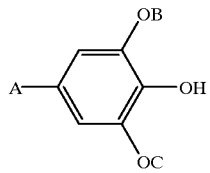

has surprisingly shown a hitherto unknown synergistic antimicrobial effect.

Thus, based on these findings the present invention provides, in a first aspect, an enzymatic antimicrobial method comprising treatment of microorganisms and/or viruses with effective amounts of laccase and said enhancers in the presence of oxygen ($O_2$) or a source of oxygen ($O_2$).

The invention is useful wherever antimicrobial treatment is needed, for example for the preservation of food, beverages, cosmetics, contact lens products, food ingredients paints or enzyme compositions; for antimicrobial treatment of e.g. on human or animal skin, hair, oral cavity, mucous membranes, wounds, bruises or in the eye; for antimicrobial treatment of laundry; and for antimicrobial treatment in connection with hard surface cleaning or disinfection.

Accordingly, in further aspects, the present invention provides a method for antimicrobial treatment of microorganisms and/or viruses present on laundry and/or in a liquid used for soaking, washing or rinsing the laundry, e.g. in a washing machine; a method for antimicrobial treatment of microorganisms and/or viruses on or in human or animal skin, hair, oral cavities, mucous membranes, teeth, eyes, wounds, bruises; a method for antimicrobial treatment of microorganisms and/or viruses on or in a cosmetic product; a method for antimicrobial treatment of microorganisms and/or viruses on or in contact lenses and a method of antimicrobial treatment of microorganisms and/or viruses present on or in a hard surface.

DETAILED DESCRIPTION OF THE INVENTION

Definitions

Figure 1:
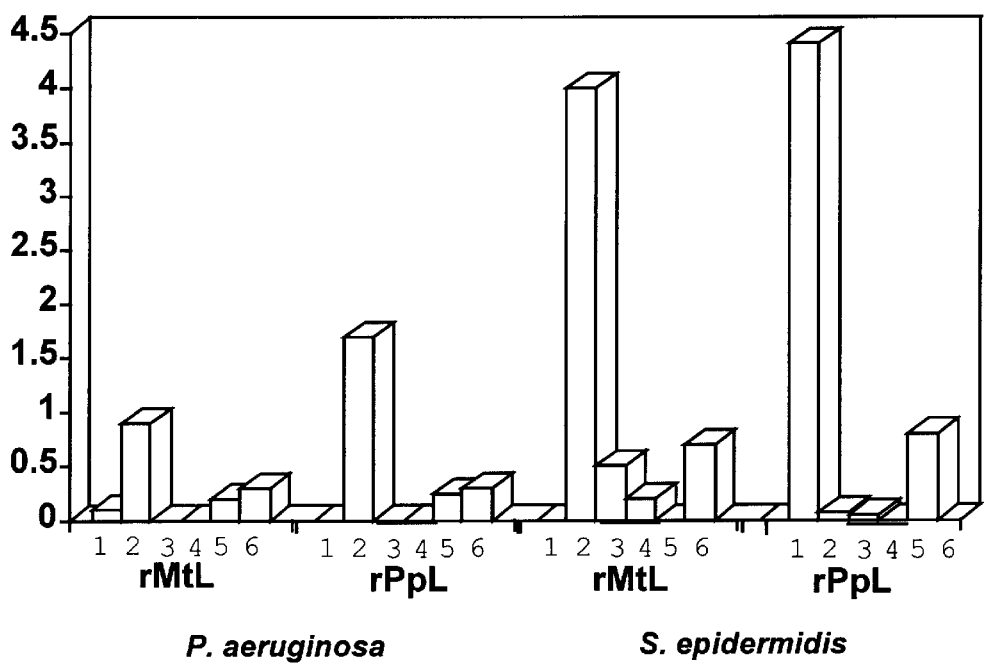
FIG. 1 shows the antimicrobial activity of different laccase systems against P. aeruginosa and S. epidermidis. Enzyme concentration used was 3 mg/L and enhancer concentration used was: 0.1 mM. The different enhancers tested were: 1=No mediator; 2=methylsyringate; 3=cinnamic acid; 4=chlorogenic acid; 5=PPT; 6=syringaldehyde. The bactericidal activity of the different combinations is indicated as log cfu/ml, i.e. the logarithm to the number of killed cfu per ml (cfu=colony forming units).

In the present context, the term antimicrobial is to be understood as bactericidal, bacteriostatic, fungicidal or fungistatic.

In the present context, the term "bactericidal" is to be understood as capable of killing bacterial cells.

In the present context, the term "bacteriostatic" is to be understood as capable of inhibiting bacterial growth, i.e. inhibiting growing bacterial cells.

In the present context, the term "fungicidal" is to be understood as capable of killing fungal cells.

In the present context, the term "fungistatic" is to be understood as capable of inhibiting fungal growth, i.e. inhibiting growing fungal cells.

The term "microorganism" denotes a virus, a bacterium or cells thereof, a fungus or cells thereof.

The term "hard surface" as used herein relates to any surface which is essentially non-permeable for microorganisms. Examples of hard surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like.

The Antimicrobial Effect

Without being bound to this theory, it is believed that the key reaction in the antimicrobial effect of the combined Laccase/enhancer system of the present invention is the oxidation of essential protein and enzyme sulphydryl groups or other cellular sites.

Laccase enzymes are able to catalyze $O_2$-dependent oxidation of an electron-donor, e.g. an enhancer. The oxidized enhancer make an electrophilic attack on microbial components, resulting in chemical modification of essential enzymes, transport systems, and other functional components. Sulphydryl groups are especially susceptible to electrophilic attack, and are usually present in higher amounts than other easily oxidized groups. Aromatic amino acid residues are also susceptible to attack. Most aspects of antimicrobial action can be correlated with chemical modification of these nucleophilic components. Antimicrobial activity is favored by influences that increase the stability of the oxidized agent, provided that these influences do not interfere with their electrophilic character, or their ability to penetrate microbial membranes. Although $O_2$ itself is an oxidizing agent, the $O_2$ molecule is stabilized and reacts only slowly with biological materials. The laccase catalyzed oxidation of the enhancer preserves the oxidizing power $O_2$ into forms that reacts more readily.

The reaction catalyzed by laccase can be written as:

$$n.O_2 + m.AH_p \rightarrow 2.n.H_2O + m.A, \quad m.p = 4n$$

where $AH_p$ and A are reduced and oxidized forms of suitable electron donors; or, in case of enhancers/agents of the formula:

The oxygen can be supplied from air either by diffusion or

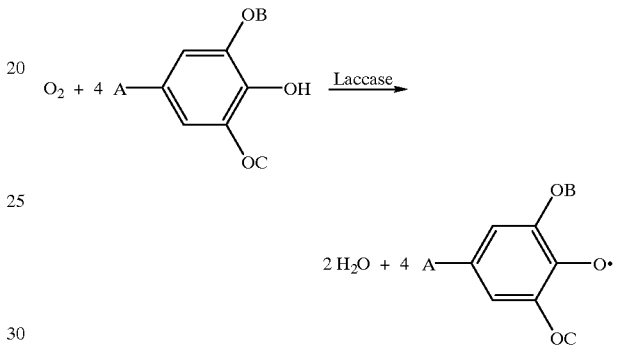

by aeration or can be generated by an oxygen liberating compound.

The antimicrobial effect may be obtained against various microorganisms like bacteria, fungi and/or virus. In particular embodiments of the invention, the antimicrobial effect may be greater towards certain strains over other strains, e.g. bacteria over fungi or vice versa or gram positive bacteria over gram negative or vice versa.

The Enzyme

Preferred are the below mentioned enzymes, especially recombinant and/or substantially purified enzymes.

In the context of this invention "laccases" include enzymes comprised by the enzyme classification E.C. 1.10.3.2.

Preferably, the laccase employed is derived from a strain of Polyporus sp., in particular a strain of *Polyporus pinisitus* or *Polyporus versicolor*, or a strain of Myceliophthera sp., e.g. *M. thermophila* or a strain of Rhizoctonia sp., in particular a strain of *Rhizoctonia praticola* or Rhizoctonia solani, or a strain of a Rhus sp., in particular *Rhus vernicifera*.

In specific embodiments of the invention the oxidoreductase is a laccase, such as a Polyporus sp. laccase especially the *Polyporus pinisitus* laccase (also called *Trametes villosa* laccase) described in WO 96/00290 (from Novo Nordisk Biotech., inc.) or a Myceliophthera sp. laccase especially the *Myceliophthera thermophila* laccase described in WO 95/33836 (from Novo Nordisk Biotech inc.).

Further, the laccase may be a Scytalidium sp. laccase, such as the *S. thermophilium* laccase described in WO 95/33837 (from Novo Nordisk Biotech inc.) or a Pyricularia sp. laccase, such as the *Pyricularia oryzae* laccase which can be purchased from SIGMA under the trade name SIGMA no. L5510, or a Coprinus sp. laccase, such as a *C. cinereus* laccase, especially a *C. cinereus* IFO 30116 laccase, or a Rhizoctonia sp. laccase, such as a *Rh. solani* laccase, especially the neutral *Rh. solani* laccase described WO 95/07988 (from Novo Nordisk A/S) having a pH optimum in the range from 6.0 to 8.5.

The laccase may also be derived from a fungi such as Collybia, Fomes, Lentinus, Pleurotus, Aspergillus, Neurospora, Podospora, Phlebia, e.g. *P. radiata* (WO 92/01046), Coriolus sp., e.g. *C. hirsitus* (JP 2-238885), or Botrytis.

The Enhancer

Various enhancers acting as electron donors for laccases for various purposes are known (e.g. WO 94/12620, WO 94/12621, WO 95/01626 and WO 96/00179). One or more enhancers being of the formula:

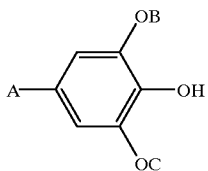

has however in the context of the invention shown to be surprisingly effective. In a preferred embodiment of the invention, A in said formula denotes a group such as —D, —CH=CH—D, —CH=CH—CH=CH—D, —CH=N—D, —N=N—D, or —N=CH—D, in which D is selected from the group consisting of —CO—E, —SO$_2$—E, —N—XY, and —N$^+$—XYZ, in which E may be —H, —OH, —R, or —OR, and X and Y and Z may be identical or different and selected from —H and —R; R being a C$_1$–C$_{16}$ alkyl, preferably a C$_1$–C$_8$ alkyl, which alkyl may be saturated or unsaturated, branched or unbranched and optionally substituted with a carboxy, sulpho or amino group; and B and C may be the same or different and selected from C$_m$H$_{2m+1}$, where m=1, 2, 3, 4 or 5.

In the above mentioned formula A may be placed meta to the hydroxy group instead of being placed in the para-position as shown.

In particular embodiments of the invention the enhancer is selected from the group having the formula:

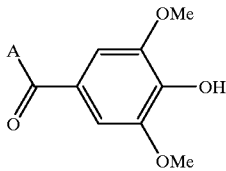

in which A is a group such as —H, —OH, —CH$_3$, —OCH$_3$, —O(CH$_2$)$_n$CH$_3$, where n=1, 2, 3, 4, 5, 6, 7 or 8.

Combinations of said enhancers may suitably be applied sequentially or simultaneously and may have additional synergistic effects, as different microorganisms may show different sensitivity towards specific enhancers. Accordingly a specific embodiment of the invention relates to an antimicrobial composition comprising a laccase enzyme (EC 1.10.3.2) and at least two different enhancers of the formula:

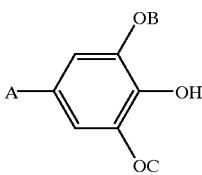

wherein A, B and C may be substituents as mentioned vide supra, and the laccase and the enhancers are present in the composition in antimicrobially effective amounts. The composition may be a solid granular or powder formulation or it may be a liquid. A solid granular composition may prepared as disclosed in U.S. Pat. No. 4,106,991, U.S. Pat. No. 4,661,452, WO 97/31088 or WO 95/33039 and may optionally be coated by methods known to the art. A liquid composition may be prepared as a stabile liquid composition by addition of conventional stabilizers, a slurry composition or a composition with the enzyme in a protected form. Protected enzymes may be prepared according to the method disclosed in EP 238,216 A or WO 97/41215.

Said enhancers are commercially available or can be made by methods known to the art.

Effective Amounts of Laccase

The Laccase may be present in the medium to be antimicrobially treated i.e. washing liquor, cosmetics, food or beverages; or in the medium used for antimicrobial treatment of other items i.e. washing liquor, disinfecting liquid, preserving liquid, foot bath etc. in 0.00001–100 mg/L, preferably 0.001–10 mg/L, e.g. 0.1–5 mg/L.

Effective Amounts of Enhancer

The Laccase may be present in the medium to be antimicrobially treated i.e. washing liquor, cosmetics, food or beverages; or in the medium used for antimicrobial treatment of other items i.e. washing liquor, disinfecting liquid, preserving liquid, foot bath etc. in 0.00001–500 mM, preferably 0.0001–5 mM, e.g. 0.001–0.050 mM.

The Medium

The medium in which the catalytic reaction between the laccase and the enhancer is intended to occur is preferably aqueous and may be a liquid, an aerosol, a gel, a paste or a slurry, depending on the intended use of the invention. The laccase and the enhancer may also be comprised, either separately or together, in solid formulations intended for preparation of said mediums.

The antimicrobial efficiency of the invention depends, inter alia, on the properties of the medium, which thus may be matched to the intended use of the invention. The properties to be matched may, inter alia, be solubility or mobility of the laccase, the enhancer and/or O$_2$, the rate of the catalytic reaction, which then again depends on e.g. pH, temperature and buffer of the medium.

The medium may also affect the half-life of radical, which the enhancer forms upon the catalytic reaction with the laccase and O$_2$ Without being limited to any theory it is presently contemplated that there is a positive correlation between the half-life of the radical in the medium and its efficiency. The half-life of the radical depends on, inter alia, the pH, the temperature and the buffer of the medium.

The medium may also comprise auxiliary agents such as wetting agents, thickening agents, buffer, stabilizers, perfume, colorants, fillers, chelators and the like (e.g. from a detergent composition).

Useful wetting agents are surfactants, i.e. non-ionic, anionic, amphoteric or zwitterionic surfactants.

As already indicated Laccases, are, among other reasons, well suited in the context of the invention since they catalyze oxidation by molecular oxygen. Thus, reactions which take place in vessels open to the atmosphere (or in other reaction vessels into which air—or for that matter another oxygen-containing gas—is introduced) and which involve an oxidase as enzyme will be able to utilize gaseous oxygen as oxidant; it may, however, be desirable to forcibly aerate the liquid medium during the reaction to ensure an adequate supply of oxygen.

pH in the Medium

Depending, inter alia, on the characteristics of the laccase and the enhancer employed, the pH in the medium employed should normally be in the range of 5–11, often preferably in the range 6–10, e.g. 6.5–8.5.

Temperature in the Medium

In numerous embodiments of the invention, temperatures in the range of 10–65° C., more preferably 30–50° C., should be employed.

Treatment Times

Treatment times depends, inter alia, on the treatment type, the type of item to be treated, the properties of the medium, e.g. temperature and pH and the type and amounts of enzyme and enhancer employed.

For preservation purposes treatment times may be in the range of depending of the expected lifetime of the item to be preserved.

For disinfecting purposes treatment times in the range of 1–120 minutes may be employed. In many cases a treatment time in the range of 5–20 minutes will be suitable.

Treatment of Laundry

As mentioned the present invention provides a method for antimicrobial treatment of microorganisms or viruses present on laundry and/or in a liquid used for soaking, washing or rinsing the laundry, e.g. in a washing machine. The laccase and the enhancer may be incorporated in a detergent composition.

Surfactant System of the Detergent Composition

The detergent compositions according to the present invention comprise a surfactant system, wherein the surfactant can be selected from non-ionic and/or anionic and/or cationic and/or ampholytic and/or zwitterionic and/or semipolar surfactants.

The surfactant is typically present at a level from 0.1% to 60% by weight.

The surfactant is preferably formulated to be compatible with enzyme components present in the composition. In liquid or gel compositions the surfactant is most preferably formulated in such a way that it promotes, or at least does not degrade, the stability of any enzyme in these compositions.

Preferred systems to be used according to the present invention comprise as a surfactant one or more of the non-ionic and/or anionic surfactants described herein.

Polyethylene, polypropylene, and polybutylene oxide condensates of alkyl phenols are suitable for use as the non-ionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available non-ionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with about 1 to about 25 moles of ethylene oxide are suitable for use as the non-ionic surfactant of the non-ionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available non-ionic surfactants of this type include Tergitol™ 15-S-9 (The condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA 050 (the condensation product of $C_{12}$–$C_{14}$ alcohol with 5 moles of ethylene oxide) marketed by Hoechst. Preferred range of HLB in these products is from 8–11 and most preferred from 8–10.

Also useful as the non-ionic surfactant of the surfactant systems of the present invention are alkylpolysaccharides disclosed in U.S. Pat. No. 4,565,647, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glycosyl moieties (optionally the hydrophobic group is attached at the 2-, 3-, 4-, etc. positions thus giving a glucose or galactose as opposed to a glycoside or galactoside). The intersaccharide bonds can be, e.g., between the one position of the additional saccharide units and the 2-, 3-, 4-, and/or 6-positions on the preceding saccharide units.

The preferred alkylpolyglycosides have the formula

$R^2O(C_nH_{2n}O)_t(glycosyl)_x$ wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glycoside (attachment at the 1-position). The additional glycosyl units can then be attached between their 1-position and the preceding glycosyl units 2-, 3-, 4-, and/or 6-position, preferably predominantly the 2-position.

The condensation products of ethylene oxide with a hydrophobic base formed by the condensation of propylene oxide with propylene glycol are also suitable for use as the additional non-ionic surfactant systems of the present invention. The hydrophobic portion of these compounds will preferably have a molecular weight from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic™ surfactants, marketed by BASF.

Also suitable for use as the non-ionic surfactant of the non-ionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of non-ionic surfactant include certain of the commercially available Tetronic™ compounds, marketed by BASF.

Preferred for use as the non-ionic surfactant of the surfactant systems of the present invention are polyethylene oxide condensates of alkyl phenols, condensation products of primary and secondary aliphatic alcohols with from about 1 to about 25 moles of ethyleneoxide, alkylpolysaccharides, and mixtures hereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred non-ionic surfactants are polyhydroxy fatty acid amide surfactants of the formula

wherein $R^1$ is H, or $R^1$ is $C_{1-4}$ hydrocarbyl, 2-hydroxyethyl, 2-hydroxypropyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is straight $C_{11-15}$ alkyl or $C_{16-18}$ alkyl or alkenyl chain such as coconut alkyl or mixtures thereof, and Z is derived from a reducing sugar such as glucose, fructose, maltose or lactose, in a reductive amination reaction.

Highly preferred anionic surfactants include alkyl alkoxylated sulphate surfactants. Examples hereof are water soluble salts or acids of the formula $RO(A)_m SO_3 M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulphates as well as alkyl propoxylated sulphates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulphate ($C_{12}$–$C_{18}$E(1.0)M), $C_{12}$–$C_{18}$ alkyl polyethoxylate (2.25) sulphate ($C_{12}$–$C_{18}$(2.25)M, and $C_{12}$–$C_{18}$ alkyl polyethoxylate (3.0) sulphate ($C_{12}$–$C_{18}$E(3.0)M), and $C_{12}$–$C_{18}$ alkyl polyethoxylate (4.0) sulphate ($C_{12}$–$C_{18}$E(4.0)M), wherein M is conveniently selected from sodium and potassium.

Suitable anionic surfactants to be used are alkyl ester sulphonate surfactants including linear esters of $C_8$–$C_{20}$ carboxylic acids (i.e., fatty acids) which are sulphonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulphonate surfactant, especially for laundry applications, comprise alkyl ester sulphonate surfactants of the structural formula:

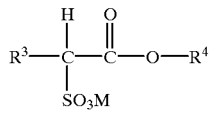

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulphonate. Suitable salt-forming cations include metals such as sodium, potassium, and lithium, and substituted or unsubstituted ammonium cations, such as monoethanolamine, diethonolamine, and triethanolamine. Preferably, $R^3$ is $C_{10}$–$C_{16}$ alkyl, and $R^4$ is methyl, ethyl or isopropyl. Especially preferred are the methyl ester sulphonates wherein $R^3$ is $C_{10}$–$C_{16}$ alkyl.

Other suitable anionic surfactants include the alkyl sulphate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16}$–$C_{18}$ alkyl chains are preferred for higher wash temperatures (e.g. above about 50° C.).

Other anionic surfactants useful for detersive purposes can also be included in the laundry detergent compositions of the present invention. Theses can include salts (including, for example, sodium, potassium, ammonium, and substituted ammonium salts such as mono- di- and triethanolamine salts) of soap, $C_8$–$C_{22}$ primary or secondary alkanesulphonates, $C_8$–$C_{24}$ olefinsulphonates, sulphonated polycarboxylic acids prepared by sulphonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulphonates, fatty acyl glycerol sulphonates, fatty oleyl glycerol sulphates, alkyl phenol ethylene oxide ether sulphates, paraffin sulphonates, alkyl phosphates, isethionates such as the acyl isethionates, N-acyl taurates, alkyl succinamates and sulphosuccinates, monoesters of sulphosuccinates (especially saturated and unsaturated $C_{12}$–$C_{18}$ monoesters) and diesters of sulphosuccinates (especially saturated and unsaturated $C_6$–$C_{12}$ diesters), acyl sarcosinates, sulphates of alkylpolysaccharides such as the sulphates of alkylpolyglycoside (the non-ionic non-sulphated compounds being described below), branched primary alkyl sulphates, and alkyl polyethoxy carboxylates such as those of the formula $RO(CH_2CH_2O)_k$—$CH_2COO$-M+ wherein R is a $C_8$–$C_{22}$ alkyl, k is an integer from 1 to 10, and M is a soluble salt forming cation. Resin acids and hydrogenated resin acids are also suitable, such as rosin, hydrogenated rosin, and resin acids and hydrogenated resin acids present in or derived from tall oil.

Alkylbenzene sulphonates are highly preferred. Especially preferred are linear (straight-chain) alkyl benzene sulphonates (LAS) wherein the alkyl group preferably contains from 10 to 18 carbon atoms.

Further examples are described in "Surface Active Agents and Detergents" (Vol. I and II by Schwartz, Perrry and Berch). A variety of such surfactants are also generally disclosed in U.S. Pat. No. 3,929,678, (Column 23, line 58 through Column 29, line 23, herein incorporated by reference).

When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the non-ionic and/or anionic surfactants other than those already described herein.

Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected form the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOHCHOHCOR^6CHOHCH_2OH$, wherein $R^6$ is any hexose or hexose polymer having a molecular weight less than about 1000, and hydrogen when y is not 0; $R^5$ is the same as $R^4$ or is an alkyl chain, wherein the total number of carbon atoms or $R^2$ plus $R^5$ is not more than about 18; each y is from 0 to about 10, and the sum of the y values is from 0 to about 15; and X is any compatible anion.

Highly preferred cationic surfactants are the water soluble quaternary ammonium compounds useful in the present composition having the formula:

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{4O})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$, particularly where the alkyl group is a mixture of chain lengths derived from coconut or palm kernel fat or is derived synthetically by olefin build up or OXO alcohols synthesis.

Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is

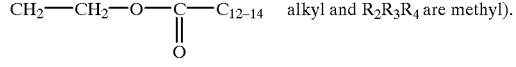

di-alkyl imidazolines [compounds of formula (i)].

Other cationic surfactants useful herein are also described in U.S. Pat. No. 4,228,044 and in EP 000 224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulphonate, sulphate. See U.S. Pat. No. 3,929,678 (column 19, lines 18–35) for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulphonium compounds. See U.S. Pat. No. 3,929,678 (column 19, line 38 through column 22, line 48) for examples of zwitterionic surfactants.

When included therein, the laundry detergent compositions of the present invention typically comprise from 0.2% to about 15%, preferably from about 1% to about 10% by weight of such zwitterionic surfactants.

Semi-polar non-ionic surfactants are a special category of non-ionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulphoxides containing one alkyl moiety from about 10 to about 18 carbon atoms and a moiety selected from the group consisting of alkyl and hydroxyalkyl moieties of from about 1 to about 3 carbon atoms.

Semi-polar non-ionic detergent surfactants include the amine oxide surfactants having the formula:

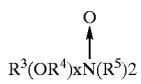

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3: and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar non-ionic surfactants.

Builder System

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphonic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenle-enschrift 2,446,686, and 2,446,487, U.S. Pat. No. 3,935,257 and the sulphinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2,-ethane tetracarboxylates, 1,1,3,3-propane tetracarboxylates containing sulpho substituents include the sulphosuccinate derivatives disclosed in British Patent Nos. 1,398, 421 and 1,398,422 and in U.S. Pat. No. 3,936,448, and the sulphonated pyrolyzed citrates described in British Patent No. 1,082,179, while polycarboxylates containing phosphone substituents are disclosed in British Patent No. 1,439,000.

Alicyclic and heterocyclic polycarboxylates include cyclopentane-cis,cis-cis-tetracarboxylates, cyclopentadien-ide pentacarboxylates, 2,3,4,5-tetrahydro-furan-cis, cis, cis-tetracarboxylates, 2,5-tetrahydro-furan-cis, discarboxylates, 2,2,5,5,-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic polycarboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelator for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2EDDS$ and $Na_4EDDS$. Examples of such preferred magnesium salts of EDDS include MgEDDS and $Mg_2EDDS$. The magnesium salts are the most preferred for inclusion in compositions in accordance with the invention.

Preferred builder systems include a mixture of a water-insoluble aluminosilicate builder such as zeolite A, and a water soluble carboxylate chelating agent such as citric acid.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated form each other by not more than two carbon atoms.

Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition. Preferred levels of builder for liquid detergents are from 5% to 30%.

Enzymes

Preferred detergent compositions, in addition to the enzyme preparation of the invention, comprise other enzyme(s) which provides cleaning performance and/or fabric care benefits.

Such enzymes include proteases, lipases, cutinases, amylases, cellulases, peroxidases, other oxidases (e.g. laccases).

Proteases: Any protease suitable for use in alkaline solutions can be used. Suitable proteases include those of animal, vegetable or microbial origin. Microbial origin is preferred. Chemically or genetically modified mutants are included. The protease may be a serine protease, preferably an alkaline microbial protease or a trypsin-like protease. Examples of alkaline proteases are subtilisins, especially those derived from Bacillus, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the Fusarium protease described in WO 89/06270.

Preferred commercially available protease enzymes include those sold under the trade names Alcalase, Savinase, Primase, Durazym, and Esperase by Novo Nordisk A/S (Denmark), those sold under the trade name Maxatase, Maxacal, Maxapem, Properase, Purafect and Purafect OXP by Genencor International, and those sold under the trade name Opticlean and optimase by Solvay Enzymes. Protease enzymes may be incorporated into the compositions in accordance with the invention at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Lipases: Any lipase suitable for use in alkaline solutions can be used. Suitable lipases include those of bacterial or fungal origin. Chemically or genetically modified mutants are included.

Examples of useful lipases include a *Humicola lanuginosa* lipase, e.g., as described in EP 258 068 and EP 305 216, a *Rhizomucor miehei* lipase, e.g., as described in EP 238 023, a Candida lipase, such as a *C. antarctica* lipase, e.g., the *C. antarctica* lipase A or B described in EP 214 761, a *Pseudomonas* lipase such as a *P. alcaligenes* and *P. pseudoalcaligenes* lipase, e.g., as described in EP 218 272, a *P. cepacia* lipase, e.g., as described in EP 331 376, a *P. stutzeri* lipase, e.g., as disclosed in GB 1,372,034, a *P. fluorescens* lipase, a *Bacillus* lipase, e.g., a *B. subtilis* lipase (Dartois et al., (1993), Biochemica et Biophysica acta 1131, 253–260), a *B. stearothermophilus* lipase (JP 64/744992) and a *B. pumilus* lipase (WO 91/16422).

Furthermore, a number of cloned lipases may be useful, including the *Penicillium camembertii* lipase described by Yamaguchi et al., (1991), Gene 103, 61–67), the *Geotricum candidum* lipase (Schimada, Y. et al., (1989), J. Biochem., 106, 383–388), and various Rhizopus lipases such as a *R. delemar* lipase (Hass, M. J et al., (1991), Gene 109, 117–113), a *R. niveus* lipase (Kugimiya et al., (1992), Biosci. Biotech. Biochem. 56, 716–719) and a *R. oryzae* lipase.

Other types of lipolytic enzymes such as cutinases may also be useful, e.g., a cutinase derived from *Pseudomonas mendocina* as described in WO 88/09367, or a cutinase derived from *Fusarium solani* pisi (e.g. described in WO 90/09446).

Especially suitable lipases are lipases such as M1 Lipase™, Luma fast™ and Lipomax™ (Genencor), Lipolase™ and Lipolase Ultra™ (Novo Nordisk A/S), and Lipase P "Amano" (Amano Pharmaceutical Co. Ltd.).

The lipases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Amylases: Any amylase ($\alpha$ and/or $\beta$) suitable for use in alkaline solutions can be used. Suitable amylases include those of bacterial or fungal origin. Chemically or genetically modified mutants are included. Amylases include, for example, $\alpha$-amylases obtained from a special strain of *B. licheniformis*, described in more detail in GB 1,296,839. Commercially available amylases are Duramyl™, Termamyl™, Fungamyl™ and BAN™ (available from Novo Nordisk A/S) and Rapidase™ and Maxamyl P™ (available from Genencor).

The amylases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Cellulases: Any cellulase suitable for use in alkaline solutions can be used. Suitable cellulases include those of bacterial or fungal origin. Chemically or genetically modified mutants are included. Suitable cellulases are disclosed in U.S. Pat. No. 4,435,307, which discloses fungal cellulases produced from *Humicola insolens*. Especially suitable cellulases are the cellulases having colour care benefits. Examples of such cellulases are cellulases described in European patent publication No. 0 495 257.

Commercially available cellulases include Celluzyme™ produced by a strain of *Humicola insolens*, (Novo Nordisk A/S), and KAC-500(B)™ (Kao Corporation).

Cellulases are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Peroxidases/Oxidases: Peroxidase enzymes are used in combination with hydrogen peroxide or a source thereof (e.g. a percarbonate, perborate or persulphate). Oxidase enzymes are used in combination with oxygen. Both types of enzymes are used for "solution bleaching", i.e. to prevent transfer of a textile dye from a dyed fabric to another fabric when said fabrics are washed together in a wash liquor, preferably together with an enhancing agent as described in e.g. WO 94/12621 and WO 95/01426. Suitable peroxidases/oxidases include those of plant, bacterial or fungal origin. Chemically or genetically modified mutants are included.

Peroxidase and/or oxidase enzymes are normally incorporated in the detergent composition at a level of from 0.00001% to 2% of enzyme protein by weight of the composition, preferably at a level of from 0.0001% to 1% of enzyme protein by weight of the composition, more preferably at a level of from 0.001% to 0.5% of enzyme protein by weight of the composition, even more preferably at a level of from 0.01% to 0.2% of enzyme protein by weight of the composition.

Mixtures of the above mentioned enzymes are encompassed herein, in particular a mixture of a protease, an amylase, a lipase and/or a cellulase.

The enzyme of the invention, or any other enzyme incorporated in the detergent composition, is normally incorporated in the detergent composition at a level from 0.00001% to 2% of enzyme protein by weight of the composition, preferably at a level from 0.0001% to 1% of enzyme protein by weight of the composition, more preferably at a level from 0.001% to 0.5% of enzyme protein by weight of the composition, even more preferably at a level from 0.01% to 0.2% of enzyme protein by weight of the composition.

Bleaching agents: Additional optional detergent ingredients that can be included in the detergent compositions of the present invention include bleaching agents such as PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional added components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483, 781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetra-acetylethylenediamine (TAED), nonanoyloxybenzene-sulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulphonate, C9(6-nonanamido caproyl) oxybenzenesulphonate and C10 (6-decanamido caproyl) oxybenzenesulphonate or mixtures thereof. Also suitable activators are acylated citrate esters such as disclosed in European Patent Application No. 91870207.7.

Useful bleaching agents, including peroxyacids and bleaching systems comprising bleach activators and peroxygen bleaching compounds for use in cleaning compositions according to the invention are described in application U.S. Ser. No. 08/136,626.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Publication EP 0 537 381.

Bleaching agents other than oxygen bleaching agents are also known in the art and can be utilised herein. One type of non-oxygen bleaching agent of particular interest includes photo-activated bleaching agents such as the sulphonated zinc and/or aluminium phthalocyanines. These materials can be deposited upon the substrate during the washing process. Upon irradiation with light, in the presence of oxygen, such as by hanging clothes out to dry in the daylight, the sulphonated zinc phthalocyanine is activated and, consequently, the substrate is bleached. Preferred zinc phthalocyanine and a photo-activated bleaching process are described in U.S. Pat. No. 4,033,718. Typically, detergent composition will contain about 0.025% to about 1.25%, by weight, of sulphonated zinc phthalocyanine.

Bleaching agents may also comprise a manganese catalyst. The manganese catalyst may, e.g., be one of the compounds described in "Efficient manganese catalysts for low-temperature bleaching", Nature 369, 1994, pp. 637–639.

Suds suppressors: Another optional ingredient is a suds suppressor, exemplified by silicones, and silica-silicone mixtures. Silicones can generally be represented by alkylated polysiloxane materials, while silica is normally used in finely divided forms exemplified by silica aerogels and xerogels and hydrophobic silicas of various types. Theses materials can be incorporated as particulates, in which the suds suppressor is advantageously releasably incorporated in a water-soluble or water-dispersible, substantially non surface-active detergent impermeable carrier. Alternatively the suds suppressor can be dissolved or dispersed in a liquid carrier and applied by spraying on to one or more of the other components.

A preferred silicone suds controlling agent is disclosed in U.S. Pat. No. 3,933,672. Other particularly useful suds suppressors are the self-emulsifying silicone suds suppressors, described in German Patent Application DTOS 2,646,126. An example of such a compound is DC-544, commercially available form Dow Corning, which is a siloxaneglycol copolymer. Especially preferred suds controlling agent are the suds suppressor system comprising a mixture of silicone oils and 2-alkyl-alkanols. Suitable 2-alkyl-alkanols are 2-butyl-octanol which are commercially available under the trade name Isofol 12 R.

Such suds suppressor system are described in European Patent Publication EP 0 593 841.

Especially preferred silicone suds controlling agents are described in European Patent Application No. 92201649.8. Said compositions can comprise a silicone/silica mixture in combination with fumed nonporous silica such as Aerosil®.

The suds suppressors described above are normally employed at levels of from 0.001% to 2% by weight of the composition, preferably from 0.01% to 1% by weight.

Other components: Other components used in detergent compositions may be employed such as soil-suspending agents, soil-releasing agents, optical brighteners, abrasives, bactericides, tarnish inhibitors, coloring agents, and/or encapsulated or non-encapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulation materials include N-Lok manufactured by National Starch. The N-Lok encapsulating material consists of a modified maize starch and glucose. The starch is modified by adding mono-functional substituted groups such as octenyl succinic acid anhydride.

Anti-redeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably form 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2' disulphonate, disodium 4,-4'-bis-(2-morpholino-4-anilino-s-triazin-6-ylamino-stilbene-2:2' -disulphonate, disodium 4,4'-bis-(2,4-dianilino-s-triazin-6-ylamino)stilbene-2:2' -disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2' disulphonate, di-so-dium 4,4'bis(2-anilino-4-(1-methyl-2-hydroxyethylamino)-s-triazin-6-ylamino)stilbene-2,2'disulphonate, sodium 2(stilbyl-4"-(naphtho-1',2':4,5)-1,2,3,-triazole-2"-sulphonate and 4,4'-bis(2-sulphostyryl)biphenyl.

Other useful polymeric materials are the polyethyleneglycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in U.S. Pat. Nos. 4,116,885 and 4,711,730 and EP 0 272 033. A particular preferred polymer in accordance with EP 0 272 033 has the formula:

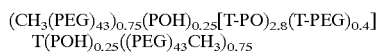

$(CH_3(PEG)_{43})_{0.75}(POH)_{0.25}[T\text{-}PO)_{2.8}(T\text{-}PEG)_{0.4}]$
$T(POH)_{0.25}((PEG)_{43}CH_3)_{0.75}$ where PEG is —$(OC_2H_4)O$—, PO is $(OC_3H_6O)$ and T is $(pOOC_6H_4CO)$.

Also very useful are modified polyesters as random copolymers of dimethyl terephthalate, dimethyl sulphoisophthalate, ethylene glycol and 1,2-propanediol, the end groups consisting primarily of sulphobenzoate and secondarily of mono esters of ethylene glycol and/or 1,2-propanediol. The target is to obtain a polymer capped at both end by sulphobenzoate groups, "primarily", in the present context most of said copolymers herein will be endcapped by sulphobenzoate groups. However, some copolymers will be less than fully capped, and therefore their end groups may consist of monoester of ethylene glycol and/or 1,2-propanediol, thereof consist "secondarily" of such species.

The selected polyesters herein contain about 46% by weight of dimethyl terephthalic acid, about 16% by weight of 1,2-propanediol, about 10% by weight ethylene glycol, about 13% by weight of dimethyl sulfobenzoic acid and about 15% by weight of sulphoisophthalic acid, and have a molecular weight of about 3.000. The polyesters and their method of preparation are described in detail in EP 311 342.

Softening agents: Fabric softening agents can also be incorporated into laundry detergent compositions in accordance with the present invention. These agents may be inorganic or organic in type. Inorganic softening agents are exemplified by the smectite clays disclosed in GB-A-1 400898 and in U.S. Pat. No. 5,019,292. Organic fabric softening agents include the water insoluble tertiary amines as disclosed in GB-A1 514 276 and EP 0 011 340 and their combination with mono $C_{12}$–$C_{14}$ quaternary ammonium salts are disclosed in EP-B-0 026 528 and di-long-chain amides as disclosed in EP 0 242 919. Other useful organic ingredients of fabric softening systems include high molecular weight polyethylene oxide materials as disclosed in EP 0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Polymeric dye-transfer inhibiting agents: The detergent compositions according to the present invention may also comprise from 0.001% to 10%, preferably from 0.01% to 2%, more preferably form 0.05% to 1% by weight of polymeric dye-transfer inhibiting agents. Said polymeric dye-transfer inhibiting agents are normally incorporated into detergent compositions in order to inhibit the transfer of dyes from colored fabrics onto fabrics washed therewith. These polymers have the ability of complexing or adsorbing the fugitive dyes washed out of dyed fabrics before the dyes have the opportunity to become attached to other articles in the wash.

Especially suitable polymeric dye-transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

Addition of such polymers also enhances the performance of the enzymes according the invention.

The detergent composition according to the invention can be in liquid, paste, gels, bars or granular forms.

Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

Granular compositions according to the present invention can also be in "compact form", i.e. they may have a relatively higher density than conventional granular detergents, i.e. form 550 to 950 g/l; in such case, the granular detergent compositions according to the present invention will contain a lower amount of "Inorganic filler salt", compared to conventional granular detergents; typical filler salts are alkaline earth metal salts of sulphates and chlorides, typically sodium sulphate; "Compact" detergent typically comprise not more than 10% filler salt. The liquid compositions according to the present invention can also be in "concentrated form", in such case, the liquid detergent compositions according to the present invention will contain a lower amount of water, compared to conventional liquid detergents. Typically, the water content of the concentrated liquid detergent is less than 30%, more preferably less than 20%, most preferably less than 10% by weight of the detergent compositions.

The compositions of the invention may for example, be formulated as hand and machine laundry detergent compositions including laundry additive compositions and compositions suitable for use in the pre-treatment of stained fabrics, rinse added fabric softener compositions, and compositions for use in general household hard surface cleaning operations and dishwashing operations.

The following examples are meant to exemplify compositions for the present invention, but are not necessarily meant to limit or otherwise define the scope of the invention.

In the detergent compositions, the abbreviated component identifications have the following meanings:

| | |
|---|---|
| LAS: | Sodium linear $C_{12}$ alkyl benzene sulphonate |
| TAS: | Sodium tallow alkyl sulphate |
| XYAS: | Sodium $C_{1X}$–$C_{1Y}$ alkyl sulphate |
| SS: | Secondary soap surfactant of formula 2-butyl octanoic acid |
| 25EY: | A $C_{12}$–$C_{15}$ predominantly linear primary alcohol condensed with an average of Y moles of ethylene oxide |
| 45EY: | A $C_{14}$–$C_{15}$ predominantly linear primary alcohol condensed with an average of Y moles of ethylene oxide |
| XYEZS: | $C_{1X}$–$C_{1Y}$ sodium alkyl sulphate condensed with an average of Z moles of ethylene oxide per mole |
| Non-ionic: | $C_{13}$–$C_{15}$ mixed ethoxylated/propoxylated fatty alcohol with an average degree of ethoxylation of 3.8 and an average degree of propoxylation of 4.5 sold under the trade name Plurafax LF404 by BASF GmBH |
| CFAA: | $C_{12}$–$C_{14}$ alkyl N-methyl glucamide |
| TFAA: | $C_{16}$–$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula $\delta$-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Poly-acrylate: | Polyacrylate homopolymer with an average molecular weight of 8,000 sold under the trade name PA30 by BASF GmBH |
| Zeolite A: | Hydrated Sodium Aluminosilicate of formula $Na_{12}(AlO_2SiO_2)_{12}.27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2.H_2O_2$ |
| PB4: | Anhydrous sodium perborate tetrahydrate |
| Per-carbonate: | Anhydrous sodium percarbonate bleach of empirical formula $2Na_2CO_3.3H_2O_2$ |
| TAED: | Tetraacetyl ethylene diamine |
| CMC: | Sodium carboxymethyl cellulose |
| DETPMP: | Diethylene triamine penta (methylene phosphonic acid), marketed by Monsanto under the Trade name Dequest 2060 |
| PVP: | Polyvinylpyrrolidone polymer |
| EDDS: | Ethylenediamine-N,N'-disuccinic acid, [S,S] isomer in the form of the sodium salt |
| Suds Suppressor: | 25% paraffin wax Mpt 50° C., 17% hydrophobic silica, 58% paraffin oil |
| Granular Suds Suppressor: | 12% Silicone/silica, 18% stearyl alcohol, 70% starch in granular form |

-continued

| | |
|---|---|
| Sulphate: | Anhydrous sodium sulphate |
| HMWPEO: | High molecular weight polyethylene oxide |
| TAE 25: | Tallow alcohol ethoxylate (25) |

Detergent Example I

A granular fabric cleaning composition in accordance with the invention may be prepared as follows:

| | |
|---|---|
| Sodium linear $C_{12}$ alkyl benzene sulphonate | 6.5 |
| Sodium sulphate | 15.0 |
| Zeolite A | 26.0 |
| Sodium nitrilotriacetate | 5.0 |
| Enzyme of the invention | 0.1 |
| PVP | 0.5 |
| TAED | 3.0 |
| Boric acid | 4.0 |
| Perborate | 18.0 |
| Phenol sulphonate | 0.1 |
| Minors | Up to 100 |

Detergent Example II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme of the invention | 0.1 |
| TAED | 6.0 |
| Percarbonate | 22.0 |
| EDDS | 0.3 |
| Granular suds suppressor | 3.5 |
| water/minors | Up to 100% |

Detergent Example III

Granular fabric cleaning compositions in accordance with the invention which are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10 |
| Citric acid | 2.5 | 3.0 |
| Zeolite A | 32.1 | 25.0 |

-continued

| | | |
|---|---|---|
| Na-SKS-6 | — | 9.0 |
| MA/AA | 5.0 | 5.0 |
| DETPMP | 0.2 | 0.8 |
| Enzyme of the invention | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinylimidazole and vinylpyrrolidone | — | 0.2 |
| Perborate | 1.0 | — |
| Phenol sulphonate | 0.2 | — |
| Water/Minors | Up to 100% | |

Detergent Example IV

Granular fabric cleaning compositions in accordance with the invention which provide "Softening through the wash" capability may be prepared as follows:

| | | |
|---|---|---|
| 45A5 | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme of the invention | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

Detergent Example V

Heavy duty liquid fabric cleaning compositions in accordance with the invention may be prepared as follows:

| | I | II |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme of the invention | 0.10 | 0.05 |
| Coco-alkyl dimethyl hydroxy ethyl ammonium chloride | — | 3.0 |
| Smectite clay | — | 5.0 |
| PVP | 2.0 | — |
| Water/Minors | Up to 100% | |

Treatment of Human or Animal Moieties

The invention provides a method for antimicrobial treatment of microorganisms or viruses present on or in human or animal skin, hair, oral cavities, mucous membranes, teeth, eyes, wounds or bruises.

Thus the invention may be useful for disinfection, e.g. treatment of acne or other skin infections, infections in the eye or the mouth, microbial growth on feet, in armpits; teeth (oral care), wounds, bruises and the like. The treatment may be applied by use of an aerosol, liquid, emulsion, gel, slurry, paste or solid comprising said laccase and said enhancer.

Treatment of Cosmetics, Food or Beverages or Other Products

The invention may be useful for preservation of food, beverages, cosmetics such as lotions, creams, gels, ointments, soaps, shampoos, conditioners, antiperspirants, deodorants, mouth wash, contact lens products, foot bath products; enzyme formulations, or food ingredients. The invention may be applied to the unpreserved food, beverages, cosmetics, food ingredients in an amounts effective for obtaining the desired antimicrobial effect.

Treatment of Contact Lenses

The invention may be useful for cleaning and/or antimicrobial treatment of contact lenses.

Treatment of a Hard Surface

In general it is contemplated that the present invention provides a method, which is useful for antimicrobial treatment of any hard surface as defined earlier. The treatment may be applied for general disinfection purposes, e.g. disinfection of hospital wards, operation rooms, rooms for food processing or other facilities, which require disinfection. The hard surface can also be a process equipment member of a cooling tower, a water treatment plant, a dairy, a processing plant for food or food additives, a chemical or pharmaceutical process plant. The hard surface may also be a medical device or a water sanitation equipment. Accordingly, the invention provides an antimicrobial method, which is useful in a conventional cleaning-in-place (C-I-P) system. The laccase and the enhancer employed in the context of the invention may, through a medium, be brought in contact with the surface in question and should be present in amounts, which is has an antimicrobial effect.

Conservation/Preservation of Paints

Conservation of paint products in cans has in the art been accomplished by adding non-enzymatic organic biocides to the paints. In the context of the invention paint is construed as a substance comprising a solid coloring matter dissolved or dispersed in a liquid vehicle such as water, organic solvent and/or oils, which when spread over a surface, dries to leave a thin colored, decorative and/or protective coating. Typically isothiazoliones, such as 5-chlor-2-methyl-4-thiazoli-3-on, has been added to the paint as biocides at dosages in the range of about 0.05–0.5% to inhibit/prevent microbial growth in the paint. The method of the invention can however suitably be applied in this field, thereby solving the problem of the ever present environmental bio-hazards of using toxic organic biocides by replacing these toxic biocides with environmentally compatible enzymes. Thus the invention provides a method for conservation of a paint comprising contacting said paint with a laccase and one or more enhancers of the invention. Further the invention provides a paint composition comprising a laccase and one or more enhancers of the invention.

The paint is preferably a water based paint, i.e. the solids of the paint is dispersed in an aqueous solution. The paint may contain 0–20 % organic solvent, preferable 0–10%, e.g. 0–5%.

The enzyme may be added the paint in an amount of 0.0001–100 mg active enzyme protein per litre paint, preferable 0.001–10 mg/L, e.g. 0.01–1 mg/L, while the enhancer may be added in an amount of 10–500 µM, preferably 25–250 µM, e.g. 100 µM of the paint composition.

The invention is illustrated by the following non-limiting examples.

EXAMPLE 1

Antibacterial Activity of Laccases with Different Enhancers

The antimicrobial activity (i.e. bactericidal activity) of recombinant Myceliophthera laccase (rMtL, WO 95/33836) and recombinant Polyporus laccase (rPpL, WO 96/00290), was tested at pH 6 by use of methylsyringate (MeS), cinnamic acid, chlorogenic acid, syringaldehyd and ppt as enhancer.

Bactericidal activity was evaluated in 0.05 M MES-buffer (2-[N-morpholino]ethanesulfonic acid) (pH 6), which were flushed with air for 5 min before filter sterilisation. The bactericidal activity was determined against *Pseudomonas aeruginosa* (ATCC10145) and *Staphylococcus epidermidis* (DSM20042). Cells were grown in Tryptone Soya Broth (Oxoid CM129) at 30° C. for 24 h and diluted in the MES-buffer to a final cell concentration of approximately $10^4$ cfu/ml. The cell suspensions were mixed with laccase (3 mg/L) and enhancer (0.1 mM) for 20 min at 40° C. The bactericidal activity was determined by incubation in Malthus. Detection times measured by the Malthus instrument were converted to cfu/ml by a calibration curve. Either direct or indirect Malthus measurements were used when enumerating total survival cells (Malthus Flexi M2060, Malthus Instrument Limited). By the direct measurements, the cell metabolism was determined by conductance measurements in the growth substrate. By the indirect measurements, 3 ml of growth medium was transferred to the outer chamber of the indirect Malthus cells, and 0.5 ml of sterile KOH (0.1 M) was transferred to the inner chamber. The cell suspensions were after enzyme treatment transferred to the outer chamber of the Malthus cell. As cells are growing in the outer chamber they produce $CO_2$ which will dissolve in the KOH in the inner chamber and thereby change the conductance of the KOH. The amount of $CO_2$ formed by the respiring cells surviving the enzyme treatment was used for estimating the number of viable cells. When the conductance change is measurable by the Malthus, a detection time (dt) will be recorded. The dt's were converted to colony counts by use of a calibration curve relating cfu/ml to dt (Johansen et al. 1995. Journal of Applied Bacteriology 78:297–303, Johansen et al. 1997, Applied and Environmental Microbiology 63:3724–3728).

Bactericidal activity (log(cfu/ml)=the logarithm to the number of killed cells) was obtained with rPpL and rMtL at pH=6, laccase=3 mg/L and enhancer 0.1 mM using methylsyringate (MeS) as enhancer. None of the other enhancers resulted in bactericidal activity (FIG. 1; 1=no enhacer; 2=methylsyringate; 3=cinnamic acid; 4=chlorogenic acid; 5=PPT; 6=syringaldehyde) at these experimental conditions, however, the bactericidal activity of a laccase/enhancer system depends inter alia on pH etc., thus the other enhancer may be favourably at e.g. high pH.

The bactericidal activity of rMtL/MeS or rPpL/MeS was particularly pronounced against *S. epidermidis* (FIG. 1) which was 100% killed (pH 6) by the rPpL/MeS and only a few cells survived the treatment with rMtL/MeS. Whereas the bactericidal activity against *P. aeruginosa* was observed as a cell reduction of 1–2 log units (FIG. 1).

EXAMPLE 2

Bactericidal Activity of Myceliophthera Laccase and Methylsyringate

Antimicrobial activity (i.e. bactericidal activity) of Myceliophthera laccase (rMtL) and methylsyringate (MeS) was determined using a $3^2$ factorial design at pH 6 at 40° C. in MES-buffer as described in example 1, however, a higher cell concentration was used ($10^7$–$10^8$ cfu/ml). Tested rMtL levels was 0–2,5–5 mg/L and MeS levels was 0–5–10 mM.

Figure 2:
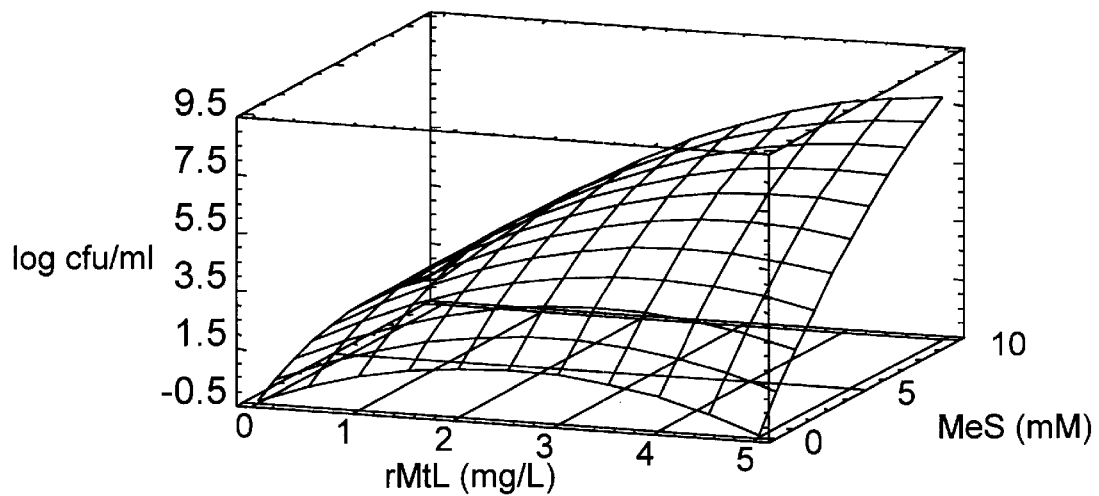
FIG. 2 shows a response surface plot for the bactericidal activity (given as the logarithm to the number of killed cfu per ml) of rMtL and MeS against Pseudomonas aeruginosa at pH 6, 40° C.

Bactericidal activity against *P. aeruginosa* ATCC10145 was obtained at MeS concentrations between 5–10 mM. Increasing the rMtL concentration from 2.5 to 5 mg/L resulted in a decreased bactericidal activity, thus the optimal concentration of enzyme will be below 5 mg/L for a bactericidal activity against *P. aeruginosa* at these particular conditions. The bactericidal activity obtained at high MeS concentrations at pH 6 was very close to a 100% bactericidal activity (FIG. 2). At pH 4, a 100% bactericidal activity was obtained.

The Gram-positive strain, *S. epidermidis*, was killed 100% by rMtL/MeS treatment at pH 5–6 and MeS concentrations above 0.5 mM. MeS was not bactericidal against the two test-organisms, in the used concentrations, unless combined with laccase.

EXAMPLE 3

Optimum pH for the Antimicrobial Activity of Laccase/methylsyringate

Antimicrobial activity (i.e. bactericidal activity) of rMtL and rPpL with MeS as enhancer was determined at pH 4–10 by use of the following buffer systems; homopipes (pH 4 and 5), MES (pH 6), HEPES (pH 7 and 8), HEPES/CAPS (pH 9) and CAPS (pH 10). Bactericidal activity was evaluated against *Staphylococcus epidermidis* at 40° C. as described in Example 1.

Figure 3:
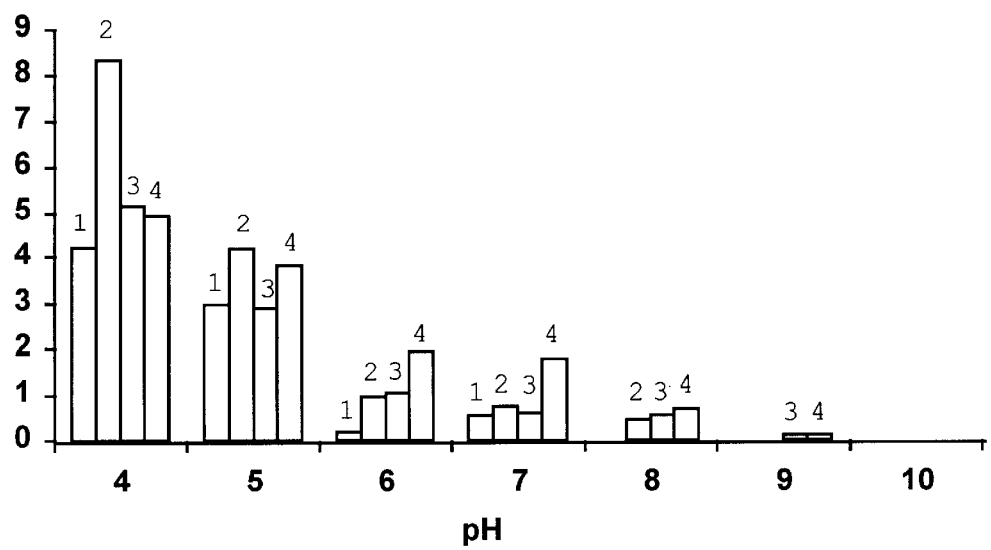
FIG. 3 shows the bactericidal activity (given as the logarithm to the number of killed cfu per ml) of laccases and methylsyringate against *Staphylococcus epidermidis* depending on pH. Laccase concentration=2 mg/L; temperature=40° C.; treatment time=20 minutes. Different laccases and MeS concentrations were used: 1=rPpL+25 mM MeS; 2=rPpL+50 mM MeS; 3=rMtL+25 mM MeS; 4=rMtL+50 mM MeS.

Both rPpL and rMtL have bactericidal activity at low pH (FIG. 3; 1=(rPpL=2 mg/l and MeS=25 mM); 2=(rPpL=2 mg/l and MeS=50 mM), 3=(rMtL=2 mg/l and MeS=25 mM); 4=(rMtL=2 mg/l and MeS=50 mM)). The bactericidal activity of rPpL and rMtL increased at decreasing pH-values, however, at the tested concentrations of MeS the bactericidal activity was limited at pH values above 5.

A significant bactericidal activity can be obtained at higher pH values by increasing the MeS concentration, thus bactericidal activity was obtained against S. epidermidis at pH 9 by use of e.g. rMtL=5 mg/L and MeS=5 mM.

Bactericidal activity can be obtained at different conditions (pH, temperature etc.) by selecting a laccase and an enhancer, which are active at the particular desired conditions.

EXAMPLE 4

Antimicrobial Activity of Myceliophthera and Polyporus Laccase Using Different Syringates Antimicrobial activity (i.e. bactericidal activity) of Myceliophthera laccase (rMtL) and Polyporus laccase (rPpL) was determined against *Staphylococcus epidermidis* at pH 6 in MES-buffer as described in example 1, the laccases was used in the concentration of 3 mg/L. Acetosyringon, methylsyringate, ethylsyringate, butylsyringate and laurylsyringate were evaluated as electron-donors in the concentration of 0.2 mM.

Figure 4:
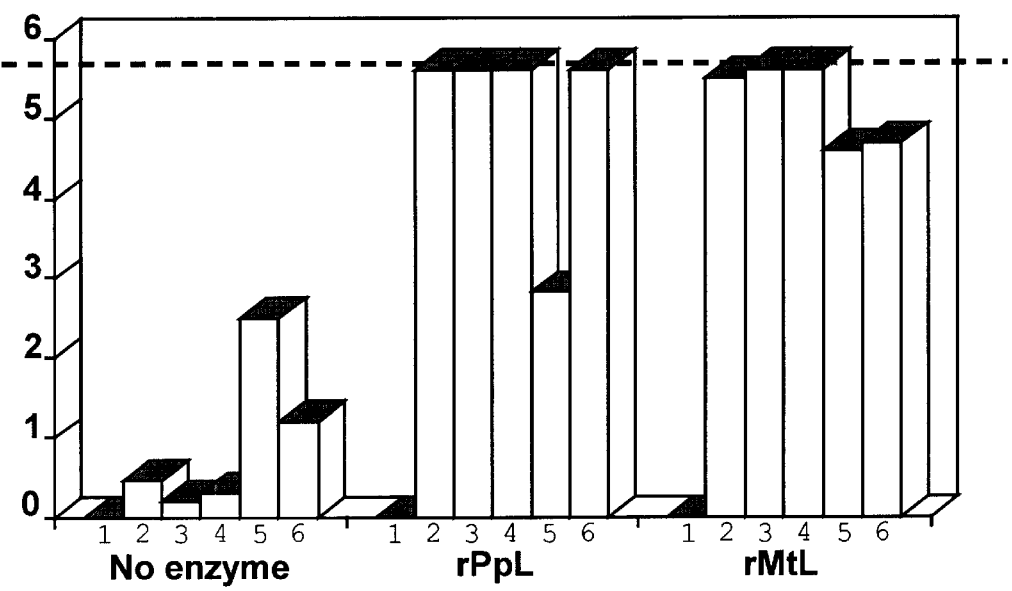
FIG. 4 shows bactericidal activity (given as the logarithm to the number of killed cfu per ml) of different syringate-compounds against *S. epidermidis* in combination with rMtL, rPpL or no laccase. Laccase concentrations were 3 mg/L; enhancer concentrations were 0.2 mM; temperature= 40° C.; pH=6; treatment time=20 minutes. Enhancers tested were: 1=no enhancer; 2=methylsyringate; 3=ethylsyringate; 4=butylsyringate; 5=laurylsyringate; 6=acetosyringon. The dashed line indicates complete kill of the tested microorganism.

All of the syringate compounds had bactericidal activity when combined with laccase. Laurylsyringate and acetosyringon did also show bactericidal activity without laccase, however, the bactericidal activity was significantly increased when laccase was added (FIG. 4; 1=no enhancer; 2=methylsyringate; 3=ethylsyringate; 4=butylsyringate; 5=laurylsyringate; 6=acetosyringone; dashed line=total kill).

Acetosyringon, methylsyringate, ethylsyringate and butylsyringate resulted in a 100% bactericidal activity against *S. epidermidis* when combined with Polyporus laccase. Whereas the bactericidal activity obtained with Myceliophthera laccase and acetosyringon was decreased compared to both the activity of Polyporus laccase and the activity obtained with the other syringate compounds. The different syringate-compounds were also evaluated against *Pseudomonas aeruginosa* which are more resistant than *S. epidermidis*. Acetosyringon was found to be the most bactericidal enhancer against *P. aeruginosa*.

EXAMPLE 5

Synergistic Effects by Combinations of Different Enhancers

The sensitivity of various microorganisms depends on the used enhancer, thus a broad spectrum of antimicrobial activity may be obtained by combining the different enhancers and applying them simultaneously. The total antimicrobial activity against a mixed culture of different microorganisms is expected to be significantly increased if a mix of enhancers is used.

It is contemplated that the enhancers are tested in a sub-lethal concentration (less than 100 % bactericidal activity), and tested in different combinations against microorganisms with different physiology. Synergistic effects may be determined by a multi-factorial experiment with a laccase and enhancers like eg acetosyringon, methylsyringate, ethylsyringate, butylsyringate and laurylsyringate.

EXAMPLE 6

Synergistic Antimicrobial Effect by Combination of Two Enhancers

Antimicrobial activity of laccases with two enhancers was determined against *Pseudomonas aeruginosa* (ATCC 10145) and *Staphylococcus epidermidis* (DSM 20042) at pH 6 as described in example 1. Methylsyringate and acetosyringon was used as enhancers and the laccase was rPpL (1 mg/L) and the antimicrobial activity was determined by use of a $3^2$ factorial experimental design.

Figure 5:
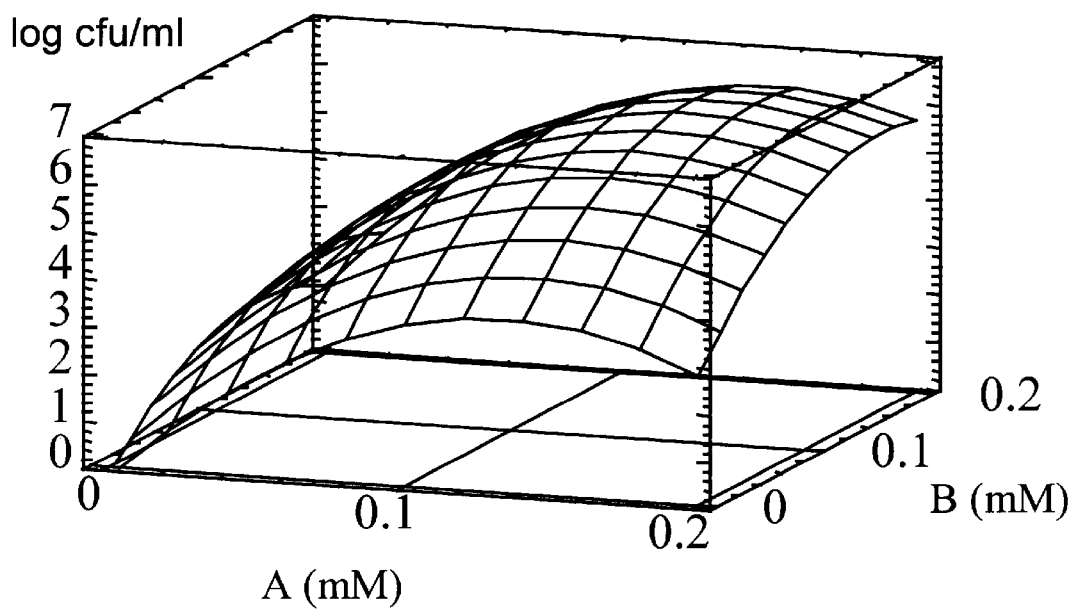
FIG. 5 shows a response surface plot for the bactericidal activity on *Pseudomonas aeruginosa* (given as the logarithm to the number of killed cfu per ml) of rPpL (1 mg/L) and methylsyringate and acetosyringon at pH 6, 40° C.

A synergistic antimicrobial activity was found when combining the two enhancers (FIG. 5; A=methylsyringate; B=Acetosyringon). Acetosyringon resulted in a cell reduction of *P. aeruginosa* of approximately 1.5 log units, methylsyringate resulted in a cell reduction of approximately 3 log units, whereas the combination resulted in a total kill of the test organism corresponding to a cell reduction of approximately 6–7 log units (FIG. 5).

EXAMPLE 7

Conservation of Paint

Conservation of a paint may be achieved by preparing a paint sample comprising the enzymatic antimicrobial system by adding an amount of laccase and enhancer, e.g. 1 mg Myceliophthera laccase and 10 μmoles of methylsyringate (sterile filtered), to 100 mL sterile water based paint in a sterile jar. To this paint sample and to a 100 mL sterile reference sample of paint without the enzyme system is now added 200 μL $10^8$ cfu/ml mixed culture sample of Pseudomonas sp. and Bacillus sp. The cultures are mixed into the paints and the jars are closed and placed at 30 or 40° C. After 3 or 4 days using conventional techniques, a sample is taken from each jar and plated on an agar plate, and growing colonies from both samples are counted. This procedure is repeated for approximately 10 times (30 or 40 days) and the colony counts from the paint sample containing the enzyme system are compared with the count from the reference sample.

What is claimed is:

1. A method for antimicrobial treatment of microorganisms and/or viruses, said method comprising treating said microorganisms and/or viruses with an effective amount of a fungal laccase (EC 1.10.3.2) enzyme and at least two enhancers in the presence of oxygen, the enhancers having the formula:

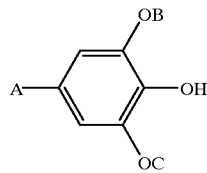

in which formula A is a group selected from —D, —CH=CH—D, —CH=CH—CH=CH—D, —CH=N—D, —N=N—D, or —N=CH—D, in which D is selected from the group consisting of —CO—E, —SO$_2$—E, —N—XY, and —N$^+$—XYZ, in which E is —H, —OH, —R, or —OR, and X and Y and Z may be identical or different and selected from —H and —R; R is C$_1$–C$_{16}$ alkyl which may be saturated or unsaturated, branched or unbranched and optionally substituted with a carboxy, sulpho or amino group; and B and C may be the same or different and selected from C$_m$H$_{2m+1}$ where 1≦m≦5.

2. An antimicrobial composition comprising a laccase enzyme (EC 1.10.3.2) and at least two different enhancers of the formula:

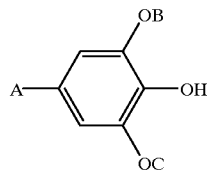

in which formula A is a group selected from —D, —CH=CH—D, —CH=CH—CH=CH—D, —CH=N—D, —N=N—D, or —N=CH—D, in which D is selected from the group consisting of —CO—E, —SO$_2$—E, —N—XY, and —N$^+$—XYZ, in which E is —H, —OH, —R, or —OR, and X and Y and Z may be identical or different and selected from —H and —R; R is C$_1$–C$_{16}$ alkyl which may be saturated or unsaturated, branched or unbranched and optionally substituted with a carboxy, sulpho or amino group; and B and C may be the same or different and selected from C$_m$H$_{2m+1}$ where 1≦m≦5.

3. The method according to claim 1, in which each of said at least two enhancers has the formula:

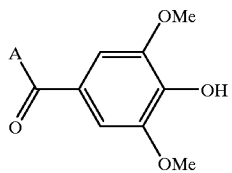

in which A is a group selected from —H, —OH, —CH$_3$, —OCH$_3$, —O(CH$_2$)$_n$CH$_3$, where n=1, 2, 3, 4, 5, 6, 7 or 8.

4. The method according to claim 1, wherein the treatment comprises use of three different enhancers simultaneously.

5. The method according to claim 1, wherein the laccase is obtained from a fungus selected from the group consisting of Myceliophthera species, Polyporus species, Coprinus species, Rhizoctonia species, Scytalidium species and Pyricularia sp.

6. The method according to claim 5, wherein the laccase is obtained from the fungus *Myceliophthera thermophila* or *Polyporus pinisitus*.

7. The method according to claim 1, for antimicrobial treatment of microorganisms and/or viruses present on laundry and/or in a liquor used for soaking, washing or rinsing the laundry.

8. The method according to claim 7, wherein the laundry is treated in a washing machine.

9. The method according to claim 1, for antimicrobial treatment of microorganisms and/or viruses present on human or animal skin, hair, oral cavity, mucous membranes, teeth, eyes, wounds or bruises.

10. The method according to claim 1, for antimicrobial treatment of microorganisms and/or viruses in a cosmetic product.

11. The method according to claim 1, for antimicrobial treatment of contact lenses.

12. The method according to claim 1, for antimicrobial treatment of a hard surface.

13. The method according to claim 12, wherein the hard surface is a facility which requires disinfection.

14. The method according to claim 13, wherein the facility is a hospital room, a room for processing of food or food additives, a room for water treatment, a room for paper and/or pulp processing or a room for chemical or pharmaceutical processing.

15. The method according to claim 12, wherein the hard surface is a process equipment within a cooling tower, a water treatment plant, a dairy, a processing plant for food or food additives, a processing plant for paper and/or pulp, or a chemical or pharmaceutical process plant.

16. The method according to claim 12, wherein the hard surface is a surface of water sanitation equipment.

17. The method according to claim 12, wherein the hard surface is a surface of a medical device.

18. The method according to claim 1, for antimicrobial treatment in a cleaning-in-place (C-I-P) system.

19. The method according to claim 1 for conserving an aqueous based paint comprising contacting said paint with a laccase (EC 1.10.3.2) and said at least two enhancers.

20. A composition comprising a paint wherein said paint comprises a solid coloring matter dissolved or dispersed in a liquid vehicle which, when spread over a surface, dries to leave a thin, decorative, and/or protective coating, a laccase (EC 1.10.3.2) and at least two enhancers, the enhancers having the formula

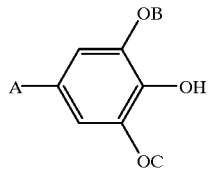

in which formula A is a group selected from —D, —CH=CH—D, —CH=CH—CH=CH—D, —CH=N—D, —N=N—D, or —N=CH—D, in which D is selected from the group consisting of —CO—E, —SO$_2$—E, —N—XY, and —N$^+$—XYZ, in which E is —H, —OH, —R, or —OR, and X and Y and Z may be identical or different and selected from —H and —R; R is C1–C16 alkyl which may be saturated or unsaturated, branched or unbranched and optionally substituted with a carboxy, sulpho or amino group; and B and C may be the same or different and selected from C$_m$H$_{2m+1}$ where $1 \leq m \leq 5$.

* * * * *